United States Patent [19]

Mauger et al.

[11] Patent Number: 5,728,403
[45] Date of Patent: Mar. 17, 1998

[54] COATING TECHNOLOGY FOR TASTE MASKING ORALLY ADMINISTERED BITTER DRUGS

[75] Inventors: John W. Mauger, Salt Lake City, Utah; Dennis H. Robinson, Omaha, Nebr.

[73] Assignee: The Board of Regents of the University of Nebraska, Lincoln, Nebr.

[21] Appl. No.: 317,695

[22] Filed: Oct. 5, 1994

[51] Int. Cl.$^6$ ............................................ A61K 9/14
[52] U.S. Cl. ........................ 424/486; 424/498; 424/484; 424/469
[58] Field of Search ........................ 424/486, 498, 424/484, 469

[56] References Cited

U.S. PATENT DOCUMENTS

| | | | |
|---|---|---|---|
| 4,650,663 | 3/1987 | Peters . | |
| 4,865,851 | 9/1989 | James et al. | 424/498 |
| 5,082,667 | 1/1992 | Van Scoik | 424/469 |
| 5,160,742 | 11/1992 | Mazer et al. | 424/469 |
| 5,380,535 | 1/1995 | Geyer et al. | 424/484 |

FOREIGN PATENT DOCUMENTS

93/17667  9/1993  WIPO ................ A61K 9/16

*Primary Examiner*—Thurman K. Page
*Assistant Examiner*—William E. Benston, Jr.
*Attorney, Agent, or Firm*—Zarley, McKee, Thomte, Voorhees & Sease

[57] ABSTRACT

A pharmaceutical coating for taste masking oral medications is described which includes a unique combination of triglycerides and a polymer. The triglyceride mixture melts at body temperature and the copolymer causes the coating to dissolve upon reaching the acidic environment of the stomach.

9 Claims, No Drawings

COATING TECHNOLOGY FOR TASTE MASKING ORALLY ADMINISTERED BITTER DRUGS

BACKGROUND OF THE INVENTION

The present invention relates to an improved coating for taste masking orally-administered bitter drugs and method for making the same.

The bitter after taste of many drugs which are orally administered, such as tablets, capsules or suspensions, often contributes to patient non-compliance in taking medicine. For many, the disagreeable taste of tablets or capsules causes difficulties in swallowing or causes patients to avoid taking their medication completely. The result is patients not receiving the optimal therapeutic value of their medication.

In addition, since elderly and pediatric patients often experience difficulty in swallowing tablets or capsules, these bitter drugs are often administered as a powder suspended in a flavored liquid via a pharmaceutical suspension. Since the drug is in a ground-up form in a suspension, the objectionable taste is increased since there is greater surface area of the drug presented for taste. In many cases, the objectionable taste cannot be circumvented by use of flavors and sweetening agents added to the pharmaceutical suspension.

Current state of the art taste masking technology uses microencapsulation techniques which rely primarily on polymer coating materials. These polymers are known to be permeable to aqueous solvents. Upon exposure to an aqueous environment, drug leaching is a frequent occurrence with these coatings since they are greatly porous and therefore permeable to water. In addition, their effectiveness for taste-masking purposes is acknowledged as being less than perfect.

Therefore, a primary object of the present invention is the provision of an improved coating for taste masking orally administered drugs and a method for making the same.

A further object of the present invention is the provision of an improved pharmaceutical coating which is non-permeable for taste masking purposes.

A further object of the present invention is the provision of an improved coating for taste masking orally administered drugs which will maintain its integrity during the brief transit period in the mouth but release the medication in the gastric fluid of the stomach.

A further object of the present invention is the provision of an improved coating for taste masking orally administered drugs that will dissolve at body temperature.

A still further object of the present invention is the provision of an improved coating for taste masking orally administered drugs and a method for making the same which is easily applied, economical in manufacture, and efficient in use.

SUMMARY OF THE INVENTION

The present invention involves the use of triglycerides in combination with a polymer as a coating for masking the taste of orally administered drugs. The triglyceride which can be a mixture is one which melts at body temperature. The polymer is one which causes the coating to dissolve at a pH of 5.5. Upon oral administration, the coating will remain intact during the brief transit in the mouth but then release the medication upon reaching the gastric fluid of the stomach.

In preparation, the triglycerides and polymer are dissolved together in an organic solvent. A drug to be coated is then suspended in this solution. After evaporating the organic solvent, remaining organic solvent is then removed from the coated drug using a separation technique. These steps may all be accomplished using conventional lab equipment.

The triglyceride/polymer combination prevents the drug coating from dissolving while still in the patient's mouth. The coated drug remains intact until reaching the stomach where it is immediately released upon contacting the gastric fluid.

DETAILED DESCRIPTION OF THE PREFERRED EMBODIMENT

The minimum ingredients necessary for the present invention are triglycerides which, when mixed together, melt at body temperature and a polymer, that is insoluble at pH 7.4 and soluble in the stomach (i.e. which dissolves at a pH of 5.5 or lower). Emulsifying and suspending agents are compatible as well.

In practice, the patient places the medication in his/her mouth and for that brief moment, the triglyceride portion of the coating begins to melt since it is now at body temperature. The coating remains intact, however, since the polymer portion will only dissolve once it reaches a pH of 5.5, which is much more acidic than the pH of the mouth. The medication then travels down the esophagus and enters the stomach. Once in the acidic environment of the stomach, dissolution occurs and the medication is then available for absorption by the body.

Eudragit E™ is the tradename for an FDA approved cationic copolymer based on dimethylaminoethyl methacrylates and neutral methacrylic acid esters. It dissolves in gastric juice. Any non-toxic polymer that is insoluble at pH 7.4 and soluble in the stomach would be an acceptable alternative. Such polymers are those that are subject to acid catalyzed decomposition, e.g., hydrolysis, yet are stable at neutral pH.

Fattibase™ is the tradename for an FDA approved composition of triglycerides derived from palm, palm kernel, and coconut oils. It also contains glyceryl monostearate and polyoxyl stearate as emulsifying and suspending agents, respectfully, but neither is necessary for the coating to function properly. It is the triglycerides which cause the composition to melt at body temperature.

Alternative triglycerides which may be used in the present invention are any non-toxic acids derived from vegetable oils such as coconut and palm kernel oil that have been modified by esterfication or hydrogenation. These may be mixtures of monoglycerides, diglycerides, and triglycerides of saturated acids derived from these oils. Typically, these can be derivatives of fatty acids of carbon chain length C6 to C18; in particular derivatives of lauric, myristic, and palmitic acids. These are solid to semi-solid materials at room temperature. The characteristic melting points of these triglycerides is in the range of 37°–40° C. Some examples include Cotomar® by Proctor & Gamble which consists of partially hydrogenated cottonseed oil; Wecobee FS® consisting of coconut and palm kernel oils; Witepsol E7S®; and Massa Estariorm A® by Edellett-Werke Werner Schluter of Hamburg, Germany which consists of a mixture of triglycerides, diglycerides, and monoglycerides of saturated fatty acids.

Eudragit E™ and Fattibase™ are the preferred compounds for use in the present invention since they are both already FDA approved for oral use in the production of pharmaceutical preparations. In addition, they both posses the required chemical properties, i.e. melting and dissolution points, for successful use of the invention. However, other polymers or triglyceride combinations may also be used so long as they posses the same requisite chemical properties.

The amount of triglyceride/polymer used to coat a particular drug is related to the amount and surface area of the drug being coated. The formulator will determine the amount of coating material needed to give a coat of specified thickness. The formulation from the example used 33% by weight of coating material. This ratio could be varied considerably depending on the particular size and porosity of the core material and amount to be coated. It would also depend upon the relative bitterness of the drug.

In general, triglycerides are preferred over mono or diglycerides for being more generally compatible with drugs. Triglycerides contain no free carboxyl groups and, thus, these groups are not free to chemically react with functional groups present on drugs.

Acetone is an organic solvent used for dissolving the Eudragit E™ and Fattibase™ in the example. The choice of organic solvent is related to its volatility, safety, and ability to dissolve both the triglycerides and polymer. Alcohols, such as methanol, ethanol and isopropyl, are therefore suitable as well as acetone. In addition, a co-solvent mixture, such as 50% by volume isopropyl alcohol and acetone, would be another workable possibility. The limitation for solvent use is based on toxicity considerations since some residual solvent may remain in the end product. Ethanol and acetone are the preferred solvents.

While metronidazole is used in the example, this process, in principle, could be applied to any solid drug which has a disagreeable or bitter taste when it dissolves in the mouth. Examples of classes of drugs which are problematic include but are not limited to antibiotics, analgesics, antihistamines, decongestants, antitussives, and steroids.

The coating materials may be easily applied using a variety of different methods, including spray coating and pan coating. These methods are well known in the art. As stated, the coating may be applied to any orally administered drug. For suspensions, the coating material will maintain its integrity to mask disagreeable taste in a liquid medium with a pH greater than 5.5 and stored at refrigerated temperatures.

Below is an example of a preferred combination of materials and methods for use in the present invention:

EXAMPLE

| MATERIAL | AMOUNT |
| --- | --- |
| Eudragit E ™ | 100 mg |
| Fattibase ™ | 200 mg |
| Acetone | 20 ml |
| Metronidazole | 1 gm |

METHOD
1. Dissolve 100 mg Eudragit E™ and 200 mg Fattibase™ and 20 ml acetone in an evaporating dish using low heat and stirring.
2. Suspend 1 gm metronidazole in acetone solution and place in hood. Evaporate acetone under conditions of vigorous stirring and at room temperature
3. Place coated material in a separatory funnel. Add 100 ml cold water and shake well. Rinse through the funnel with cold water and collect coated material on a filter paper. Repeat this process at least three times to remove acetone and any uncoated drug.

In the specification there has been set forth a preferred embodiment of the invention, and all those specific terms are employed, these are used in a generic and descriptive sense only and not for purposes of limitation. Changes in the form and the proportion of parts as well as in the substitution of the equivalent or contemplated as circumstances may suggest or render expedient without departing from the spirit and scope of the invention as further defined in the following claims.

What is claimed is:

1. A coating for masking the disagreeable taste of drug particles comprising:

a triglyceride mixture which melts at body temperature; and a polymer which dissolves at pH levels at or below 5.5 wherein said coating comprises approximately 33% by weight of said coated drug articles.

2. A coating according to claim 1 wherein said triglyceride mixture consists of palm, palm kernel, and coconut oil.

3. A coating according to claim 1 wherein the triglyceride mixture consists of palm, palm kernel, and coconut oil.

4. A coating according to claim 1 wherein said polymer is a copolymer.

5. A coating according to claim 4 wherein said copolymer is based on dimethylaminoethyl methacrylate and neutral methacrylic acid esters.

6. A coating according to claim 1 wherein said polymer is soluble in gastric juice at a pH of about 7.4 or less.

7. The composition of claim 1 consisting essentially of:

a disagreeable tasting drug which is coated with a triglyceride mixture which melts at body temperature; and a polymer which dissolves at pH levels at or below 5.5.

8. A coated drug according to claim 7 wherein said disagreeable tasting drug is from about 0.01 to about 1 gram of metronidazole.

9. A coating for masking the disagreeable taste of drug particles comprising:

a triglyceride mixture comprising monoglycerides, diglyceride and triglycerides from an esterified hydrogenated vegetable oil which melts at body temperature and a cationic copolymer composition comprising dimethylaminoethyl methacrylate and neutral methacrylic acid esters, which dissolves at pH levels at or below 5.5.

* * * * *